United States Patent
Peoples et al.

(10) Patent No.: US 6,207,217 B1
(45) Date of Patent: Mar. 27, 2001

(54) ANIMAL NUTRITION COMPOSITIONS

(75) Inventors: Oliver P. Peoples, Arlington, MA (US); Court Saunders, Clive, IA (US); Scott Nichols, Johnston, IA (US); Larry Beach, Des Moines, IA (US)

(73) Assignees: Pioneer Hi-Bred International, Inc., Des Moines, IA (US); Metabolix, Inc., Cambridge, MA (US)

(*) Notice: Subject to any disclaimer, the term of this patent is extended or adjusted under 35 U.S.C. 154(b) by 0 days.

(21) Appl. No.: 09/226,581

(22) Filed: Jan. 7, 1999

Related U.S. Application Data

(60) Provisional application No. 60/070,630, filed on Jan. 7, 1998.

(51) Int. Cl.⁷ .................. A23K 1/00; A23K 1/18
(52) U.S. Cl. .................. 426/635; 426/49; 426/807; 426/623; 426/630
(58) Field of Search .................. 426/49, 630, 635, 426/807, 623

(56) References Cited

U.S. PATENT DOCUMENTS

| | | | |
|---|---|---|---|
| 4,876,331 | 10/1989 | Doi | 528/361 |
| 5,107,016 | 4/1992 | Pennetreau | 560/179 |
| 5,245,023 | 9/1993 | Peoples et al. | 536/23.2 |
| 5,250,430 | 10/1993 | Peoples et al. | 435/232 |
| 5,292,860 | 3/1994 | Shiotani et al. | 528/371 |
| 5,610,041 | 3/1997 | Somerville et al. | 435/135 |
| 5,650,555 | 7/1997 | Somerville et al. | 800/205 |
| 5,663,063 | 9/1997 | Peoples et al. | 435/135 |
| 5,704,160 | 1/1998 | Bergquist et al. | 47/58 |
| 5,824,779 | 10/1998 | Koegel et al. | 530/370 |
| 6,043,063 | * 3/2000 | Kurdikar et al. | 435/135 |

FOREIGN PATENT DOCUMENTS

| | | |
|---|---|---|
| 1152916 | 8/1983 | (CA) . |
| 0 406 015 | 1/1991 | (EP) . |
| WO91/00917 | 1/1991 | (WO) . |
| WO92/09211 | 6/1992 | (WO) . |
| WO92/19747 | 11/1992 | (WO) . |
| WO93/02187 | 2/1993 | (WO) . |
| WO93/02194 | 2/1993 | (WO) . |
| WO94/12014 | 6/1994 | (WO) . |
| WO95/20614 | 8/1995 | (WO) . |
| WO95/20615 | 8/1995 | (WO) . |
| WO95/20621 | 8/1995 | (WO) . |
| WO95/33064 | 12/1995 | (WO) . |
| WO97/07229 | 2/1997 | (WO) . |
| WO97/07230 | 2/1997 | (WO) . |
| WO97/15681 | 5/1997 | (WO) . |
| WO98/46782 | 10/1998 | (WO) . |

OTHER PUBLICATIONS

Hovell et al., Br. J. Nutr., vol. 40(2), pp. 171–184, 1978.*
Eskeland et al., Br. J. Nutr., vol. 29(3), pp. 347–355, 1973.*
Abe, et al., "Biosynthesis from gluconate of a random copolyester consisting of 3–hydroxybutyrate and medium––chain–length 3–hydroxyalkanoates by Pseudomonas sp. 61–3," *Int. J. Biol. Macromol.* 16:115–19 (1994).
Amos & McInerney, "Composition of poly–β–hydroxyalkanoate from *Syntrophomonas wolfei* grown on unsaturated fatty acid substrates," *Arch. Microbiol.* 155:103–06 (1991).
Baidoo, et al., "Effect of kernel density on the apparent and true metabolizable energy value of corn for chickens," *Poult. Sci.* 70(10):2102–07 (1991).
Blanch, et al., "The nutritive value of dietary fats in relation to their chemical composition. Apparent fat availability and metabolizable energy in two–week–old chicks," *Poult. Sci.* 74(8):1335–40 (1995).
Brandl, et al., "Ability of the phototrophic bacterium *Rhodospirillum rubrum* to produce various poly (beta–hydroxyalkanoates): potential sources for biodegradable polyesters," *Int. J. Biol. Macromol.* 11:49–55 (1989).
De Smet, et al., "Characterization of intracellular inclusions formed by *Pseudomonas oleovorans* during growth on octane," *J. Bacteriol* 154:870–78 (1983).
Forni, et al., "Novel biodegradable plastics in sheep nutrition 2. Effects of NaOH pretreatment of poly(3–hydroxybutyrate–co–3–hydroxyvalerate) on in vivo digestibility and on in vitro disappearance (Rusitec)," *J. Anim. Physiol. & Anim. Nutn.* 81:41–50 (1999).
Friesen, et al., "The effect of enzyme supplementation on the apparent metabolizable energy and nutrient digestibilities of wheat, barley, oats, and rye for the young broiler chick," *Poult. Sci.* 71(10):1710–21 (1992).
Kato, et al., "Production of a novel copolyester of 3–hydroxybutyric acid with a medium–chain–length 3–hydroxyalkanoic acids by Pseudomonas sp. 61–3 from sugars," *Appl. Microbiol. Biotechnol.* 45:363–70 (1996).

(List continued on next page.)

Primary Examiner—Chhaya D. Sayala
(74) Attorney, Agent, or Firm—Arnall Golden & Gregory, LLP

(57) ABSTRACT

Compositions providing increased energy content of animal feed using plant crop biomass which include a polyhydroxyalkanoate have been developed. In one embodiment, the compositions can be prepared using conventional techniques for harvesting and processing plant crops into forms useful as animal feed, wherein the plant, or parts thereof, have accumulated PHA, preferably in excess of 2% by dry weight of the plant tissue. In a preferred embodiment, the PHA is accumulated in corn or an oilseed. The feed compositions can include the PHA-containing meal byproduct from corn or oilseed processing. In another embodiment, the PHA can be provided with the green tissue of plants, such as clover, alfalfa, sorghum, and silage corn.

14 Claims, No Drawings

OTHER PUBLICATIONS

Laurin, et al., "Methods of measuring energy utilization in broilers: effect of genetic line and presence of supplemental dietary fat," *Poult. Sci.* 64(5):969–78 (1985).

Le Borgne & Spassky, "Stereoelective polymerization of β–butyrolactone," *Polymer* 30:2312–19 (1989).

Lee, et al., "Biosynthesis of copolyesters consisting of 3–hydroxybutyric acid and medium–chain–length 3–hydroxyalkanoic acids from 1,3–butanediol or from 3–hydroxybutryrate by Pseudomonas sp. A33," *Appl. Microbiol. Biotechnol.* 42:901–909 (1995).

Lee, et al., "Metabolizable energy and amino acid availability of full–fat seeds, meals, and oils of flax and canola," *Poult. Sci.* 74(8) (1995).

Mittendorf, et al., "Synthesis of medium–chain–length polyhydroxyalkanoates in *Arabidopsis thaliana* using intermediates of peroxisomal fatty acid beta–oxidation," *Proc Natl Acad Sci USA* 95:13397–402 (1998).

Poirier, et al., "Polyhydroxybutyrate, a Biodegradable Thermoplastic, Produced in Transgenic Plants," *Science* 256:520–523 (1992).

Scott & Boldaji, "Comparison of inert markers [chromic oxide or insoluble ash (Celite)] for determining apparent metabolizable energy of wheat– or barley–based broiler diets with or without enzymes," *Poult. Sci.* 76(4):594–98 (1997).

Scott, et al., "A broiler chick bioassay for measuring the feeding value of wheat and barley in complete diets," *Poult. Sci.* 77(3):449–55 (1998).

Steinbüchel & Valentin, "Diversity of bacterial polyhydroxyalkanoic acids," *FEMS Microbiol. Lett.* 128:219–28 (1995).

Steinbüchel & Wiese, "A Pseudomonas strain accumulating polyesters of 3–hydroxybutyric acid and medium–chain–length 3–hydroxyalkanoic acids," *Appl. Microbiol. Biotechnol.* 37:691–97 (1992).

Valentin, et al., "Identification of 4–hydroxyhexanoic acid as a new constituent of biosynthetic polyhydroxyalkanoic acids from bacteria," *Appl. Microbiol. Biotechnol.* 40:710–16 (1994).

Valentin, et al., "Identification of 4–hydroxyvaleric acid as a constituent of biosynthetic polyhydroxyalkanoic acids from bacteria," *Appl. Microbiol. Biotechnol.* 36:507–14 (1992).

Valentin, et al., "Identification of 5–hydroxyhexanoic acid, 4–hydroxyaheptanoic acid and 4–hydroxyoctanoic acid as new constituents of bacterial polyhydroxyalkanoic acids," *Appl. Microbiol. Biotechnol.* 46:261–67 (1996).

Williams & Peoples, "Biodegradable plastics from plants," *Chemtech* 26:38–44 (1996).

Wiseman, et al., "Prediction of the apparent metabolizable energy content of fats fed to broiler chickens," *Poult. Sci.* 70(7):1527–33 (1991).

* cited by examiner

ANIMAL NUTRITION COMPOSITIONS

CROSS-REFERENCE TO RELATED APPLICATIONS

Priority is claimed to provisional application U.S. Ser. No. 60/070,630, filed Jan. 7, 1998, entitled "*Animnal Nutrition Compositions*" by Oliver Peoples, Court Saunders, Scott Nichols, and Larry Beach.

BACKGROUND OF THE INVENTION

The present invention generally relates to animal feed for livestock, and more particularly to improving the metabolizable energy content of that feed.

Feed is a major cost in the production of livestock for the meat industry, and a majority of the animals' diet is from grains, particularly corn, and oilseeds. Consequently, a major goal for improving the value of feed components is to increase the metabolizable energy content per volume of the feed. One example of this effort is the development of corn having a high oil content as described in U.S. Pat. No. 5,704,160 to Bergquist et al.

New and improved plant species also have been developed for other, unrelated purposes, such as the production of polymers, for example poly [(R)-3-hydroxyalkanoates] (PHAs). Methods have been developed to recover PHA from the plant biomass for further processing into plastic resins useful in a broad range of industrial and biomedical applications (Williams and Peoples, CHEMTECH 26: 38–44 (1996)). Frequently, the PHAs or their derivatives must be recovered from oilseeds of certain plant, for example using methods described in PCT applications WO 97/15681, WO 97/07230, and WO 97/07229. However, it is not economically feasible to extract the PHAs from all types of oilseeds, unless, for example, the byproducts of extraction processing, such as oil and meal, have sufficient value.

It is therefore an object of this invention to provide compositions and methods for enhancing the metabolizable energy content of animal feed products.

It is a further object of this invention to provide compositions and methods for enhancing the value of byproducts from the bioproduction of polymers.

SUMMARY OF THE INVENTION

Compositions providing increased energy content of animal feed using plant crop biomass including polyhydroxyalkanoates (PHAs) are disclosed herein. The PHA should be metabolizable and preferably is produced in transgenic bacteria or crop species. The compositions can be prepared using conventional techniques for harvesting and processing plant crops into forms useful as animal feed, wherein the plant, or parts thereof, have accumulated PHA, preferably in excess of 2% by dry weight of the plant tissue. The plant having accumulated PHAs also can be grown and consumed directly by the animal without harvesting or subsequent processing.

In a preferred embodiment, the PHA is accumulated in corn or an oilseed, such as Brassica, sunflower, soybean, cottonseed, and flax. The feed compositions can include the meal byproduct from these oil seeds. The compositions also can include feed additives, such as animal and vegetable fats, salt, lysine, choline, methionine, vitamins and minerals. In another embodiment, the PHA can be provided with the green tissue of plants such as clover, alfalfa, sorghum, and silage corn.

Methods for preparing the feed compositions are provided, along with methods for enhancing the metabolizable energy content of an animal feed product by either accumulating a metabolizable polyhydroxyalkanoate in the animal feed product, or adding the polyhydroxyalkanoate to the feed product. Also provided is a method of increasing the growth rate of an animal including the step of feeding the animal a plant part comprising a polyhydroxyalkanoate.

DETAILED DESCRIPTION OF THE INVENTION

It was discovered that PHAs can contribute to the apparent metabolizable energy in animal feed, and that PHAs are tolerated by animals. These findings have led to the compositions and methods disclosed herein. In one preferred embodiment, PHAs can be produced in transgenic plants where the PHA would not have to be extracted, but would serve as a supplemental source of energy for animal nutrition. In another preferred embodiment, the PHA biosynthetic genes can be expressed in the green tissue of plants which are used primarily as animal fodder.

I. Composition Components

The feed compositions disclosed herein are intended to provide or supplement the nutritional requirements of a variety of animals, including cattle, poultry, swine, sheep, goats, other monogastric or ruminant livestock, as well as exotic and zoo animals. The compositions include PHAs, preferably in some combination with plant crop biomass, which is any plant or part thereof that is fed to and consumed by animals. The PHAs preferably are accumulated intracellularly in the plant tissues.

A. Polyhydroxyalkanoates

Poly [(R)-3-hydroxyalkanoates] (PHAs) are biodegradable and biocompatible thermoplastic materials, produced from renewable resources. In recent years, what was viewed as a single polymer, poly-β-hydroxybutyrate (PHB), has evolved into a broad class of polyesters with different monomer compositions and a wide range of physical properties. To date around one hundred different monomers have been incorporated into the PHA polymers (Steinbuichel and Valentin, FEMS Microbiol. Lett. 128: 219–28 (1995)). It has been useful to broadly divide the PHAs into two groups according to the length of their side chains and their pathways for biosynthesis. Those with short side chains, such as polyhydroxybutyrate (PHB), a homopolymer of R-3-hydroxybutyric acid units, $$-\text{OCR}^1\text{R}^2(\text{CR}^3\text{R}^4)_n\text{CO}- \tag{1}$$

where n is 0 or an integer and $R^1$, $R^2$, $R^3$, and $R^4$ are each selected from saturated and unsaturated hydrocarbon radicals; hal- and hydroxy-substituted radicals; hydroxy radicals; halogen radicals; nitrogen-substituted radicals; oxygen-substituted radicals; and hydrogen atoms, are crystalline thermoplastics, whereas PHAs with long side chains are more elastomeric. The former have been known for about seventy years (Lemoigne & Roukhelman, 1925), whereas the latter materials were first identified in the early 1980's (deSmet et al., J. Bacteriol., 154: 870–78 (1983)). Before this designation, however, PHAs of microbial origin containing both (R)-3-hydroxybutyric acid and one or more long side chain hydroxyacid units containing from five to sixteen carbon atoms had been identified (Steinbüchel and Wiese, Appl. Microbiol. Biotechnol. 37: 691–97 (1992); Valentin et al., Appl. Microbiol. Biotechnol. 36: 507–14 (1992); Valentin et al., Appl. Microbiol. Biotechnol. 40: 710–16 (1994); Lee et al., Appl. Microbiol. Biotechnol. 42:

901–09 (1995); Kato et al., Appl. Microbiol. Biotechnol. 45: 363–70 (1996); Abe et al., Int. J. Biol. Macromol. 16: 115–19 (1994); Valentin et al., Appl. Microbiol. Biotechnol. 46: 261–67 (1996); and U.S. Pat. No. 4,876,331). A combination of the two biosynthetic pathways probably provide the hydroxyacid monomers. These latter copolymers can be referred to as PHB-co-HX. Useful examples of specific two-component copolymers include PHB-co-3-hydroxyhexanoate (Brandl et al., Int. J. Biol. Macromol. 11: 49–55 (1989); Amos and McInerey, Arch. Microbiol. 155: 103–06 (1991); and U.S. Pat. No. 5,292,860 to Shiotani et al.). Chemical synthetic methods have also been used to prepare racemic PHB copolymers of this type for applications testing (PCT applications WO 95/20614, WO 95/20615, and WO 96/20621).

The PHAs useful in the present compositions should be metabolizable. As used herein, the phrase "metabolizable polyhydroxyalkanoates" means that the PHAs can be digested by the animal to provide a source of useable energy to the animal.

PHAs useful in the animal field include compounds derived from PHA polymers by either chemical, biological or physical means. The PHA polymers or derivatives thereof may contain repeat units defined by the formula of Formula 1. These repeat units can be the same, as in a homopolymer, or can be selected from two or more units, such as in a copolymer or terpolymer. The PHA polymers may be converted to oligomers, monomers, dimers, trimers, etc., during processing of the plant biomass comprising PHA. For example, the PHA biomass may be subject to treatment with chemical agents such as acids, bases, metal ions, aqueous and organic solutions, oxidizing and reducing agents, nucleophilic and electrophilic reagents, free radicals, and/or conditions which result in elimination or rearrangement processes.

The preferred PHAs for use in the compositions disclosed herein include polyhydroxybutyrate, as well as copolymners including D-3-hydroxybutyrate, D-3-hydroxyhexanoate, D-3 hydroxyoctanoate, and/or D-3-hydroxydecanoate monomers.

B. Other Feed Components

The animal nutrition compositions includes other plant components, which can depend on the particular source of the PHA. For example, the PHA can be provided with seed meal where the PHA is produced in an oilseed. Examples of meals, which can be PHA-containing, or provided as a separate non-PHA containing component of the feed composition, include yellow corn, flax, cottonseed, canola, and sunflower. Alternately, the PHA can be provided with the green tissue of plants such as alfalfa, sorghum, and silage corn.

The compositions can include additives, for example, to supplement the animals' nutritional needs or to enhance its growth rate. These additives include animal and vegetable fats, salt, lysine, choline, methionine, vitamins and minerals. The compositions can include other components known in the art, for example, as described in *Feed Stuffs*, 70(30) (1998).

II. Making the Animal Nutrition Compositions

The compositions can be prepared using conventional techniques for harvesting and processing plant crops into forms useful as animal feed, with the additional requirement that the plant, or parts thereof, have accumulated PHA, preferably in excess of 2% by dry weight of the plant tissue. The plant having accumulated PHAs also can be grown and consumed directly by the animal without harvesting or subsequent processing. These include PHAs derived by fermentation or expression in recombinant hosts in the form in which it is expressed, partially purified or isolated and then added to the animal feeds.

A. Preparation of PHAs Generally

The PHAs can be prepared from a biological source such as a microorganism which naturally produces the PHAs or which can be induced to produced the PHAs by manipulation of culture conditions and feedstocks, or microorganisms or a higher organism such as a plant, which has been genetically engineered so that it produces PHAs. It is particularly desirable for economic reasons to be able to produce these polymers in transgenic bacteria and crop species. Such production methods are described in U.S. Pat. No. 5,245,023 to Peoples, et al.; U.S. Pat. No. 5,250,430 to Peoples, et al; U.S. Pat. No. 5,610,041 to Somerville, et al.; U.S. Pat. No. 5,650,555 to Somerville, et al., which are incorporated by reference. Other publications describing these production methods include PCT applications WO 91/00917, WO 92/19747, WO 93/02187, WO 93/02194, and WO 94/12014; Poirier et al., *Science* 256:520–23 (1992); and Mittendorf et al., *Prod. Proc. Nat'l Acta* 95: 13397–402 (1998).

When derived from plant crop biomass, the PHA biomass may be subject to crushing, grinding, agitation, heating, cooling, pressure, vacuum, sonication, centrifugation, and/or radiation treatments, and any other art recognized procedures, which are typical of alfalfa or corn biomass processing. One example of such a process is described in U.S. Pat. No. 5,824,779 to Koegel et al.

B. PHAs From Oilseeds and Other Plant Parts

In a preferred embodiment, the PHA is derived from a plant part. For example, in a more preferred embodiment, the compositions include a PHA-containing oilseed or the byproducts of oilseed processing, such as the meal. Oilseed meal frequently is utilized in the animal feed industry. Therefore one of skill in the art can readily adapt oilseed meal remaining following partial extraction of PHA from the oilseed for use in making an animal feed. PCT application WO 97/15681 describes methods for recovering a range of PHAs or their derivatives from oilseeds. A number of other approaches have also been described, such as in PCT applications WO 97/07230 and WO 97/07229.

The quantity of PHA in the animal feed depends in part on the initial amounts of PHA accumulated in the oilseed, as well as on the degree of PHA extraction, if any. Examples of oilseeds include Brassica, sunflower, soybean, cottonseed and flax. If the PHA is produced in an oilseed such as Brassica, sunflower, soybean, or cottonseed, or in corn, where the levels of PHA may not be high enough for economic extraction, etc., the PHA containing oilseed can still provide enhanced value. For example, the oil could be recovered as described PCT application WO 97/15681 and the PHA-containing meal used as an energy enhanced meal in animal feed formulations.

C. PHAs From Green Tissues

In another embodiment, the PHA can be produced in the green tissue of plants. In this method, the enzymes for PHA biosynthesis should be directed into the chloroplasts, for example by targeting the enzymes expressed from the transgenes using chloroplast targeting peptides. Methods for achieving high levels of PHB in chloroplasts are described, for example, in U.S. Pat. No. 5,610,041 to Somerville, et al.

Plants suitable for use with this approach include clover, alfalfa, sorghum, and silage corn. The PHA-containing green tissues can be processed into a form suitable for use as an animal feed using conventional processes known to those of skill in the art, as for example described in U.S. Pat. No. 5,657,621 to Mendes et al. and U.S. Pat. No. 5,653,042 to Besnard.

The present invention will be further understood by reference to the following non-limiting example.

EXAMPLE 1

Evaluation of PMB and PMO Animal Feed Compositions

Methods and Materials

Broiler chicks Apparent Metabolizable Energy (AME) model procedures were carried out to evaluate the apparent metabolizable energy of two types of PHA: polyhydroxybutyrate (PHB) and polyhydroxyoctanoate (PHO). AME model procedures are known in the art and described, for example, in Laurin, et al., *Poult. Sci.*, 64(5): 969–78 (1985); Baidoo et al., *Poult. Sci.*, 70(10): 2102–07 (1991); Wiseman et al., *Poult. Sci.*, 70(7): 1527–33 (1991); Friesen et al., *Poult. Sci.*, 71(10): 1710–21 (1992); Blanch et al., *Poult. Sci.*, 74(8): 1335–40 (1995); Lee et al., *Poult. Sci.*, 74(8): 1341–8 (1995); Scott et al., *Poult. Sci.*, 76(4): 594–98 (1997); and Scott et al., *Poult. Sci.*, 77(3): 449–55 (1998).

For this experiment, PHB was recovered from *Alcaliugenes eutrophus* cells grown in a 20 L fermenter to a cell density of greater than 150 g/L. At the end of the fermentation, the cells contained approximately 65% by weight of PHB. In order to purify the PHB granules, the cells were lysed and treated with protease in the presence of surfactant. After this treatment, the granules were recovered by centrifugation and washed extensively with distilled water, treated with hydrogen peroxide, and washed again.

PHO granules were extracted from *Psuedonionas putida* cells grown in a 20 L fermenter using octanoic acid as the sole carbon source to obtain a cell density in excess of 100 g/L. The cells contained greater than 45% by weight of the PHO polymer. Gas chromatography analysis of the composition of the PHO polymer indicated that it was a copolymer of 90% hydroxyoctanoate units and 10% hydroxyhexanoate units. The PHO granules were recovered following cell lysis, protease treatment, and centrilugation washing.

Results

Plant biomass samples were evaluated for their apparent metabolizable energy using the broiler chicks AME model. The compositions of the basal starter meal are as shown in Table 1 and 2 below. Meal samples comprising PHB or PHO were formatted to have the compositions indicated in Table 3. Samples P1 to P6 are described with reference to Table 3. Sample P1, which included additional water, and P6, which included soybean oil, were used as the negative and positive controls. Samples P2 and P3 contained polylhydroxybutyrate (PHB) and P4 and P5 contained poly(3-hydroxyoctanoate-co-3-hydroxyhexanoate) (PHO).

The results in Table 3 demonstrate that PHB and PHO provide improved energy to the broiler chicks. In addition, the results indicate that the available energy from the PHA lies in the range between carbohydrate and the oil, indicative of the intermediate oxidation state and energy content of the PHAs. The "Dietary Level" in Table 3 indicates the weight percent of the PHA (or soy oil) in the sample.

TABLE 1

Starter Basal Composition

| Actual | Adjusted | % | No | Ingredient | Cost | Low | High |
| --- | --- | --- | --- | --- | --- | --- | --- |
| 993.26 | 993.26 | 49.663 | 270 | Corn Yellow | 10.84 | 10.30 | 11.92 |
| 655.78 | 655.78 | 32.789 | 750 | Soybean meal-48% | 16.00 | 15.28 | 19.97 |
| 140.00 | 140.00 | 7.000 | 340 | An. & Veg. fat | 21.00 | 0.00 | 22.54 |
| 4.77 | 4.77 | 0.238 | 690 | Salt | 4.92 | 0.11 | 109.84 |
| 1.64 | 1.64 | 0.082 | 480 | L-Lysine-HCl | 153.05 | 14.43 | 172.43 |
| 11.43 | 11.43 | 0.572 | 485 | Limestone | 1.20 | 0.11 | 16.44 |
| 34.98 | 34.98 | 1.749 | 305 | Def. Phos. 32-18 | 14.45 | 1.62 | 84.10 |
| 1.70 | 1.70 | 0.085 | 221 | Choline CH-60% | 75.90 | 0.09 | 333.93 |
| 0.50 | 0.50 | 0.025 | 855 | Vitamin Premix | 530.00 | 0.00 | 0.00 |
| 1.50 | 1.50 | 0.075 | 830 | Trace Min. Premix | 300.00 | 0.00 | 0.00 |
| 7.70 | 7.70 | 0.385 | 300 | DL Methionine | 163.00 | 16.17 | 224.32 |
| 120.00 | 120.00 | 6.000 | 710 | Sand | 5.00 | 0.00 | 0.00 |
| 26.75 | 26.75 | 1.337 | 650 | Rice Hulls | 1.00 | -219.70 | 1.97 |

TABLE 2

Starter Basal Nutrient Values

| Nutrient | Type | Asked | Actual | Adjusted | Ingredient | Type | Asked |
| --- | --- | --- | --- | --- | --- | --- | --- |
| Weight | Equ. | 100.000 | 100.000 | 100.000 | Anim. & Veg. Fat | Max | 7.000 |
| Protein % | Min | 20.000 | 20.000 | 20.000 | Vitamin premix | Equ | 7.000 |
| Energy-kCal/lb | Min | 1400.000 | 1400.000 | 1400.000 | Trace Miner. Prx. | Equ | 0.075 |
| Lysine % | Min | 1.200 | 1.200 | 1.200 | Sand | Equ | 6.000 |
| Lysine % | Max | 1.270 | 1.200 | 1.200 | | | |
| Meth + Cyst % | Min | 1.050 | 1.050 | 1.050 | | | |

TABLE 2-continued

Starter Basal Nutrient Values

| Nutrient | Type | Asked | Actual | Adjusted | Ingredient | Type | Asked |
|---|---|---|---|---|---|---|---|
| Meth + Cyst % | Max | 1.200 | 1.050 | 1.050 | | | |
| Methionine % | Min | 0.500 | 0.716 | 0.716 | | | |
| Avail Phos % | Min | 0.450 | 0.450 | 0.450 | | | |
| Sodium % | Min | 0.200 | 0.200 | 0.200 | | | |
| Choline g/Kg | Min | 1.300 | 1.300 | 1.300 | | | |
| Calcium % | Min | 0.880 | 0.880 | 0.880 | | | |

TABLE 3

Energy Values of Meal Samples

| Treatment Number | Material Source | Dietary Level | AME Value Kcal/# | Energy Improvements Alone (Kcal/#) | Energy Improvements % Dietary Improvement |
|---|---|---|---|---|---|
| P1 | Water | none | 1423 | — | 0.00 |
| P2 | PHO | 3 | 1465 | 42 | 2.95 |
| P3 | PHO | 6 | 1512 | 89 | 6.25 |
| P4 | PHB | 3 | 1468 | 45 | 3.16 |
| P5 | PHB | 6 | 1502 | 79 | 5.55 |
| P6 | Soy oil | 3 | 1488 | 65 | 4.57 |

Modifications and variations of the present invention will be obvious to those skilled in the art from the foregoing detailed description. Such modifications and variations are intended to come within the scope of the appended claims.

We claim:

1. An animal feed composition comprising a metabolizable polyhydroxyalklanoate in an amount effective to increase the energy content of animal feed composition.

2. The animal feed composition of claim 1 wherein the polyhydroxyalkanoate is derived from a plant or part thereof.

3. The animal feed composition of claim 2 wherein the plant is selected from the group consisting of clover, corn, sorghum, and alfalfa.

4. The animal feed composition of claim 3 wherein the oilseed is selected from the group consisting of Brassica, sunflower, soybean, canola, flax, and cottonseed.

5. The animal feed composition of claim 2 wherein the polyhydroxyalkanoate is produced in an oilseed.

6. The animal feed composition of claim 1 wherein the polyhydroxyalkanoate is derived from a bacteria.

7. The animal feed composition of claim 1 wherein the polyhydroxyalkanoate is a polyhydroxybutyrate.

8. The animal feed composition of claim 1 wherein the polyhydroxyalkanoate is a copolymer including monomers selected from the group consisting of D-3-hydroxybutyrate, D-3-hydroxyhexanoate, D-3 hydroxyoctanoate, and D-3-hydroxydecanoate.

9. The animal feed composition of claim 1 further comprising components selected from the group consisting of proteins, yellow corn, oilseed meals, vegetable fats, lysine, choline, vitamins, minerals, and mixtures thereof.

10. The animal feed composition of claim 1 further comprising plant crop biomass.

11. The animal feed composition of claim 10 wherein the plant crop biomass comprises an oilseed or oilseed meal.

12. The animal feed composition of claim 10 wherein the polylhydroxyalkanoate is accumulated intracellularly in the plant tissues.

13. The animal feed composition of claim 12 wherein the plant tissue is a plant part of a plant selected from the group consisting of clover, corn, sorghum, alfalfa, and mixtures thereof.

14. The animal feed composition of claim 13 wherein the polyhydroxyalkanoate is present in the plant part in an amount greater than approximately 2% by dry weight.

* * * * *